United States Patent [19]

Fladd

[11] Patent Number: 5,422,714
[45] Date of Patent: Jun. 6, 1995

[54] DEVICE FOR COMPARING THE REFRACTIVE INDICES OF AN OPTICAL IMMERSION LIQUID AND A REFERENCE GLASS

[75] Inventor: David R. Fladd, Hannawa Falls, N.Y.
[73] Assignee: Corning Incorporated, Corning, N.Y.
[21] Appl. No.: 72,118
[22] Filed: Jun. 7, 1993
[51] Int. Cl.$^6$ ............................................. G01N 21/41
[52] U.S. Cl. .................................. 356/128; 356/361; 356/130
[58] Field of Search ............... 356/128, 130, 134, 246, 356/361

[56] References Cited

U.S. PATENT DOCUMENTS

| | | | |
|---|---|---|---|
| 3,612,696 | 10/1971 | Broerman | 356/128 |
| 3,797,940 | 3/1974 | King | 356/134 |
| 4,436,420 | 3/1984 | Depp et al. | 356/128 |
| 4,551,020 | 11/1985 | Reid et al. | 356/128 |
| 4,569,590 | 2/1986 | Karny et al. | 356/128 |
| 4,934,818 | 6/1990 | Glantschnig et al. | 356/73.1 |
| 4,952,055 | 8/1990 | Wyatt | 356/128 |
| 4,980,551 | 12/1990 | Wong | 356/440 |
| 5,151,752 | 9/1992 | Oono et al. | 356/128 |
| 5,157,454 | 10/1992 | Oka et al. | 356/130 |
| 5,305,071 | 4/1994 | Wyatt | 356/128 |

FOREIGN PATENT DOCUMENTS

| | | |
|---|---|---|
| 1035933 | 6/1954 | Germany . |
| 664754 | 1/1949 | United Kingdom . |
| 726402 | 9/1952 | United Kingdom . |

*Primary Examiner*—William Mintel
*Assistant Examiner*—Minhloan Tran
*Attorney, Agent, or Firm*—Milton M. Peterson; Clinton S. Janes, Jr.

[57] ABSTRACT

A device for quickly and accurately comparing the refractive index of an optical immersion liquid with the refractive index of a reference glass that the liquid is to be used with. The device comprises a cavity to at least partially contain the immersion liquid by the reference glass. The containment may be total, as in a hollow core, or may be between two windows composed of the reference glass and assembled in a spaced, facing relationship, one window having an inner face with a plano portion and a portion with a continuous slope, and a cavity intermediate the windows to contain the liquid being compared. The cavity is then filled with the liquid to be compared, transmitting laser light through the windows and the liquid to form an optical interference pattern. The method comprises filling the cavity in the device with the liquid being compared, allowing the unit to reach thermal equilibrium, inserting the device in the working path of an interferometer and transmitting laser light through the windows and liquid to create an optical interference pattern, measuring the optical path difference (OPD) shown by the pattern and difference the difference in refractive index $\Delta n$ from the formula $$\Delta n = \frac{OPD}{\Delta T}$$

where $\Delta T$ is the depth or height of the slope in the one window.

3 Claims, 1 Drawing Sheet

DEVICE FOR COMPARING THE REFRACTIVE INDICES OF AN OPTICAL IMMERSION LIQUID AND A REFERENCE GLASS

FIELD OF THE INVENTION

A device and method for testing the refractive index match between an optical immersion liquid and a reference glass.

BACKGROUND OF THE INVENTION

Refraction is a phenomenon which causes light rays to be bent as they are transmitted from a material of one refractive index to a material having a different index. The relative differences in refractive index within a piece of glass are a particularly important property, and must be closely controlled. These relative index differences are typically measured with laser interferometry where the index difference must be tightly controlled. Glasses requiring tight control of refractive index variation are widely used in instruments ranging from simple magnifying glasses to complex equipment, such as photolithography lens systems.

It is common practice to employ a liquid of known refractive index while measuring the relative refractive index differences with samples of optical glass. Such index-matching liquids are commercially available, and are known as optical immersion liquids. Index-matching fluids are used to fill the gap between polished glass reference flats and a rough-ground test surface. They eliminate the need to polish every test surface prior to measurements. With the test sample in the matching liquid, light is successively passed through the first reference flat, the index-matching liquid, the test sample, the index-matching liquid, and the second reference flat. A recording of the laser interference fringe pattern produced thus determines whether the desired glass quality is obtained.

It is necessary to obtain a high degree of homogeneity in optical glass during the glass production processes. Thus, the presence of inclusions or foreign materials, such as contaminants, must be avoided. Also, streaks, known as striae or cords, which may result from the glass forming, melting and/or mixing processes, are a cause for rejection. Homogeneity can be readily checked since the defects will have a different refractive index from the glass. The need for frequent checking of glass homogeneity, and for a reliable immersion fluid for this purpose, are apparent.

It has been found that variations in optical immersion liquids can occur between lots, and also due to deterioration and/or contamination on standing. Also, there are often differences in environmental conditions, such as temperature, between the usage area and the test area at which the liquid was qualified. The application in which the liquid is used may also be using a different wavelength of light than the wavelength at which the liquid was qualified. This will result in a shift of the observed refractive index of the immersion liquid between test locations.

Slight differences in index match between the immersion liquid and glass, coupled with non-flat test surfaces on the test sample, can cause significant errors in homogeneity measurements. Errors due to finishing/separation of the glass sample are commonly circularly symmetric about the disc radius. Consequently, immersion oil mismatch will cause circularly-symmetric errors in the transmitted wavefront measurement. This is especially evident in polynomial wavefront fits.

It has been shown that immersion liquids that do not have a desired refractive index may be mixed with other compatible immersion oils of different index to optimize the index of the mixture. Therefore, it would be desirable to have a quick, easy way to establish a proper mixture ratio using small amounts of immersion liquid.

It is then a basic purpose of the invention to provide a device and method to meet these needs. A specific purpose is to provide a quick, easy method of checking the relative refractive index match between an optical immersion liquid and the glass sample. Another specific purpose is to provide a means of quickly deciding a correction ratio to use in mixing a bulk quantity of optical immersion liquid to obtain a desired refractive index. A further specific purpose is to provide a quick check of refractive index match that does not delay production schedules.

SUMMARY OF THE INVENTION

The article is a device for comparing the refractive index of an optical immersion liquid with the refractive index of a reference glass that the liquid is to be used with, the device comprising two windows composed of the reference glass and assembled in a spaced, facing relationship, one window having an inner face with a plano portion and a portion with a continuous slope, and a cavity intermediate the windows to contain the liquid being compared.

The invention further resides in a method of comparing the refractive index of an optical immersion liquid with the refractive index of a reference glass that the liquid is to be used with, the method comprising at least partial containment of the immersion liquid by the reference glass, transmitting laser light through the liquid to form an optical pattern, determining the optical path difference (OPD) from the pattern, and determining the difference in refractive index $\Delta n$ from the formula $$\Delta n = \frac{OPD}{\Delta T}$$

where $\Delta T$ is the depth or height of the slope in the one window.

PRIOR ART

U.S. Pat. No. 3,612,696 (Broerman) discloses a refractometer used to measure liquid refractive indices in a liquid chromatography operation. The cell employed is relatively small, has a refracting member, and has a window in each side to transmit light. The application is to detect changes in the composition of fluid streams by monitoring the refractive index of the fluid. There is no mention of using laser interferometry to detect optical path difference. Further, there is no mention of the possibility of any glass being a candidate for use as a substrate to be matched by the liquid. Also, there is no mention of the possibility of any continuous window slope being acceptable for use in measurements.

U.S. Pat. No. 4,980,551 (Wong) discloses an infrared absorption spectra recording, sample cell having windows to provide passage of an infrared light beam. The windows have inner faces so shaped as to provide a sample space that yields light paths of different lengths. There is no suggestion of measuring the refractive index in a liquid. The purpose of the patent is to avoid interference fringes. There is no suggestion of the usage of laser interferometry for refractive index measurements, or analysis of interference fringe patterns in doing so.

German Patent No. 1,035,933 (Behrend) describes a method and apparatus for measuring the refractive index of a liquid by development of an image on a scale. There is no indication of a special glass being required. The patent does not utilize laser interferometry or interference fringes in measurements of refractive index. The patent deals with imaging properties of the "liquid lens", and not direct analysis of optical path difference induced by the refractive index mismatch.

DESCRIPTION OF THE INVENTION

Figure 1:
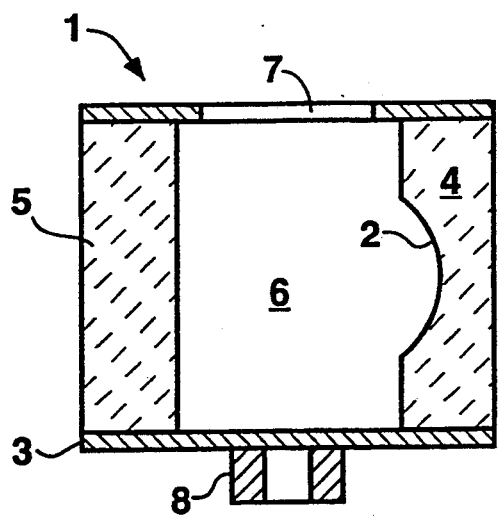
FIG. 1 is a schematic side view in cross-section showing the device of the invention.

The article of this invention is designed to provide a quick check of the relative refractive index match between an optical immersion liquid and a reference glass that the liquid is formulated to match. The device is intended to be used in conjunction with any interferometer, utilizing a collimated beam, which is set up to measure the transmitted wavefront of plano-plano glass samples.

The device utilizes optical interference patterns to compare the refractive index of an immersion liquid being tested with that of a reference glass. The reference glass must have a physical depression, or raised area of continuous slope, and a plano area within the same clear aperture for reference. A mismatch in refractive indices is observed in terms of interference fringes produced with an interferometer. The fringes may be counted manually. (2fringes=1 wavelength for double-pass interferometers) However, use of an automatic phase or fringe measuring interferometer will, of course, increase the accuracy of the measurement.

The relative index mismatch is then determined from the observed wavefront depth (Optical Path Difference) as measured with an interferometer. The determination is made using the formula $$\Delta n = \frac{OPD}{\Delta T}$$

where:
$\Delta n$=difference in refractive indices between the immersion liquid and the reference glass.
OPD=Optical Path Difference (measured by the interferometer).
$\Delta T$=the depth of the physical depression, or the height of a raised area, on the reference glass.

It is implied that, given a perfect match in refractive indices between the glass and immersion liquid, the optical path difference would be zero, and no interference fringes would be observed. A perfect match in indices will render the sloped window surface invisible in optical path difference.

The device consists of a container providing a cavity to hold a small volume of liquid. The container should be small to minimize the amount of liquid required for the measurement. Preferably the container volume should be not over 20 cubic centimeters (ccs). The container is enclosed on opposite sides by windows composed of the glass that the liquid is formulated to test, and which it should match in refractive index. Refractive index is a function of temperature and wavelength, so the liquid should be formulated to match the sample glass under the proper conditions (temperature and wavelength of the illuminating laser).

For example, the device was designed for use in fused silica production. However, it is obvious that it may be used with any liquid-optical glass combination for which comparative measurements are made. Thus, the device can be used for any optical glass and immersion liquid designed to match that glass. The requirements are that the windows be fabricated from the glass which the liquid is formulated to match, and that one of the windows have a raised area, or depressed surface, of constant slope. The range of applications of the device potentially covers all usable optical, ultraviolet, and infrared transmitting materials for which a refractive index matching, immersion liquid is available, or could be generated, and could be probed with an interferometer utilizing lasers of wavelengths in the ultraviolet, visible, and infrared ranges.

FIG. 1 is a schematic side view in cross-section showing a device generally designated 1 that employs a spherical, continuous slope 2 on the inner face of one window.

Figure 2:
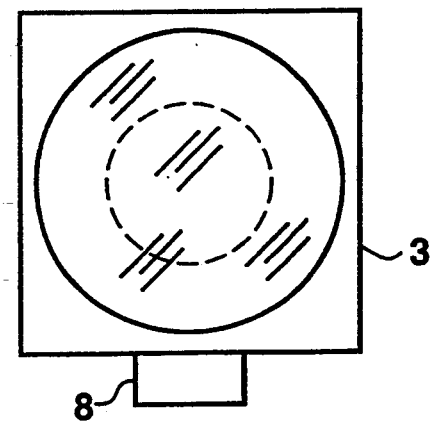
FIG. 2 is a front view of the device shown in FIG. 1.

FIG. 2 is a front view of the device looking in the direction of light travel through the device.

Device 1 comprises a structural frame 3 fabricated of a suitable material for potting glass windows. The windows may be potted in any suitable way, such as with epoxy or retaining rings.

Mounted in frame 3 are two optical windows, front window 4 and rear window 5. These windows normally are circular discs, and are fabricated from the glass whose index is to be matched by the liquid. The glass should be free of inclusions, and of sufficient homogeneity to provide the accuracy of measurement required for the application.

Windows 4 and 5 should be large enough to permit passage of sufficient light for the purpose. In general, a diameter of at least 5 cm, equivalent to an area of at least 20 cm$^2$ is adequate. The glass should have an optical polish of $\lambda/10$ on the outer face and $\lambda/5$ on the inner face. The inner face of front window 4 should have a continuous slope to permit measurements of optical path difference. This continuous slope may be provided by various contours, such as a generated sphere, a prism, or a partial wedge face. Each window may have a frame which facilitates mounting in structure 3.

Windows 4 and 5 are spaced apart to provide a cavity 6 for the immersion liquid to be checked. Cavity 6 is purposely kept small to minimize the amount of liquid required. It is desirable that it be not over 20 ccs in volume. Device 1 may be provided with an entry and exit port 7 for immersion liquid. It may also be provided with a mounting member 8 to permit mounting the device on a post or table for filling.

Figure 3:
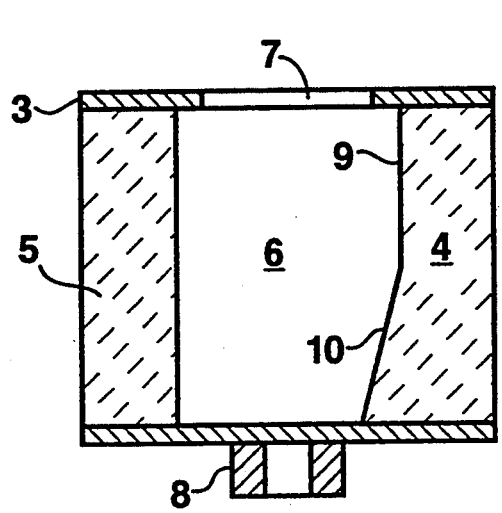
FIG. 3 is a schematic side view in cross-section of an alternate form of the functional window of the invention.

FIG. 3 is a schematic cross-section of an alternate form of functional front window 4. Window 4 has a plano portion 9 of uniform thickness. It has a second, wedge-shaped portion 10. Other possible surface configurations are apparent, and are contemplated. As in FIG. 1, rear window 5 is of uniform thickness with plano surfaces.

Figure 4:
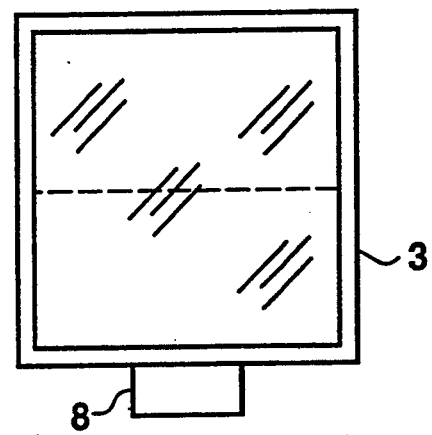
FIG. 4 is a front view of the device shown in FIG. 3.

FIG. 4 is a front view of the device in FIG. 3.

Figure 5:
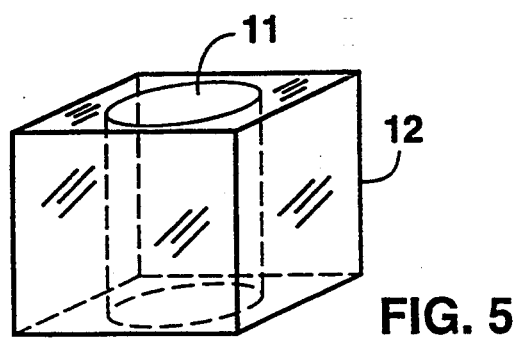
FIG. 5 is an alternate form of the invention shown in perspective.

FIG. 5 is an alternate form of the invention, wherein the immersion liquid is entirely contained in a cavity 11 by the reference glass 12. This illustrates total containment within a hollow core, such as a cylinder.

In operation, the following steps will be taken:

1. Device 1 is assembled with windows 4 and 5 of appropriate glass.
2. Device cavity 6 is sufficiently filled with a sample of the immersion liquid to be tested to cover the windows.
3. The device 1 is placed within an interferometer cavity, but out of the working beam, for thermal stabilization.
4. When the device is stabilized, it is placed in the interferometer beam and the OPD observed is measured. The measurement may be taken manually by fringe counting, or automatically by software phase or fringe analysis.
5. Index mismatch is calculated by the formula for $\Delta n$ as set forth earlier.
6. Measured amounts of compatible immersion oil of higher or lower index may be added until $\Delta n$ meets a predetermined criterion, or until fringes disappear indicating a close match.
7. The device is removed from the working interferometer beam.
8. The device cavity 6 is emptied and cleaned of all residual immersion liquid.

By way of specific example, an experiment was performed to determine the difference, if any, between the refractive indices of Corning Code 7940 Fused Silica and a matching immersion fluid used in conjunction with this product. The experiment involved producing a fused silica disc having a radius of curvature cut into one face. The depth of this curve was 5.241 mm. By comparing the number of fringes observed in an interference pattern with the known depth of the curve cut in the fused silica disc, the $\Delta n$ value could be determined. To facilitate counting fringes, the fringe pattern was magnified.

In conducting the experiment, two different oils were employed. One, an oil that had been in use, the other an oil that was unused. Also, fringes were counted both manually and using the interferometer software analysis. The results were as follows:

The measurements, and OPDs based thereon, were:

Old liquid: 16 fringes = $5.0624 \times 10^{-6}$ m OPD

New liquid (manual): 17 fringes = $5.3788 \times 10^{-6}$ m OPD

New liquid (software):

17,219 fringes = $5.44809 \times 10^{-6}$ m OPD

Values for $\Delta n$, calculated from these data were as follows:

Old liquid: $\Delta n = 0.97 \times 10^{-3}$

New liquid: $\Delta n = 1.03 \times 10^{-3}$

Software: $\Delta n = 1.04 \times 10^{-3}$

Subsequently, an improved index oil was obtained commercially which was qualified to tighter tolerances. When tested as above, a mismatch of $0.12 \times 10^{-3}$ was determined, an order of magnitude improvement.

I claim:

1. A method of comparing the refractive index of an optical immersion liquid with the refractive index of a reference glass that the liquid is to be used with, the method comprising at least partial containment of the immersion liquid by the reference glass, the reference glass comprising a window with an inner face having a plano potion and a portion with a continuous slope, transmitting laser light through the window and the liquid, thereby producing optical paths, comparing the optical path of light transmitted through the sloped potion of the window with the optical path of light transmitted through the plano; portion, observing a difference in the light paths indicating a difference in refractive indices and adding a liquid having a compensating difference in refractive index to the original liquid.

2. A method in accordance with claim 1 wherein the reference glass has the shape of a hollow core.

3. A method in accordance with claim 1 wherein the continuous slope on the window face is produced by generating a depressed surface in a portion of the inner face of the window.

* * * * *